(12) United States Patent
Senibi et al.

(10) Patent No.: US 6,925,869 B2
(45) Date of Patent: Aug. 9, 2005

(54) ULTRASONIC FUEL-GAUGING SYSTEM

(75) Inventors: Simon D. Senibi, Covington, WA (US); David M. Anderson, Issaquah, WA (US); David L. Banks, Bellevue, WA (US); James J. Childress, Mercer Island, WA (US); Mostafa Rassaian, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 31 days.

(21) Appl. No.: 10/352,635

(22) Filed: Jan. 28, 2003

(65) Prior Publication Data

US 2004/0144170 A1 Jul. 29, 2004

(51) Int. Cl.[7] .............................................. G01F 23/00
(52) U.S. Cl. ...................... 73/290 V; 73/866.5; 73/643; 73/644; 73/596
(58) Field of Search ........................... 73/290 V, 866.5, 73/643, 644, 596; 340/621

(56) References Cited

U.S. PATENT DOCUMENTS

| | | | | |
|---|---|---|---|---|
| 3,951,190 A | * | 4/1976 | Suter ...................... | 244/135 B |
| 4,389,580 A | * | 6/1983 | Bendyshe Walton et al. .... | 340/540 |
| 5,172,594 A | | 12/1992 | Dyke | |
| 5,357,486 A | * | 10/1994 | Pearce ......................... | 367/159 |
| 5,438,868 A | * | 8/1995 | Holden et al. ............ | 73/290 V |
| 5,586,085 A | * | 12/1996 | Lichte .......................... | 367/99 |
| 5,836,192 A | * | 11/1998 | Getman et al. ........... | 73/290 V |
| 6,142,015 A | * | 11/2000 | Getman et al. ........... | 73/290 V |
| 6,192,752 B1 | * | 2/2001 | Blaine ...................... | 73/290 R |
| 6,236,142 B1 | * | 5/2001 | Durkee ...................... | 310/319 |

* cited by examiner

*Primary Examiner*—Hezron Williams
*Assistant Examiner*—André K. Jackson
(74) *Attorney, Agent, or Firm*—Alston & Bird LLP

(57) ABSTRACT

The invention provides a fuel-tank system with an ultrasonic fuel-gauging system for an aircraft. The fuel-tank system includes a fuel tank, a transducer carrier tape covered with a separation barrier, and coupled to a surface of the fuel tank, and at least one ultrasonic transducer attached to the transducer carrier tape. An ultrasonic signal from at least one ultrasonic transducer is reflected from a fuel-air surface and a reflected signal is received by at least one ultrasonic transducer to determine a fuel level in the fuel tank.

17 Claims, 4 Drawing Sheets

- 410: Provide Fuel Tank Shell
- 420: Position Transducer Carrier Tape
- 430: Encase Transducer Carrier Tape with Separation Barrier

ULTRASONIC FUEL-GAUGING SYSTEM

FIELD OF THE INVENTION

This invention relates generally to fluid level measurement systems and the integration of these systems. In particular, the invention relates more specifically to an ultrasonic fuel-tank gauging system for determining the amount of fuel in a fuel tank.

BACKGROUND OF THE INVENTION

Fuel monitoring systems for aircraft typically use capacitive fuel-gauging sensors. These sensors determine the amount of fuel in a tank by measuring the pressure near the bottom of the tank relative to a measurement of pressure above the fuel-air interface, and determining the height of the fluid from the pressure differential. From the height of the fluid and knowledge of the tank geometry, the amount of fuel in the tank may be ascertained. The capacitive fuel-gauging sensors determine the differential pressure by deflecting a diaphragm or other deformable element, and measuring the deflection with a capacitive pickoff mechanism. Such sensing mechanisms typically require entry at one or more points in the fuel tank and associated tubing to access the pressure ports for pressure measurements, along with wiring or cabling that may be inside the fuel tank or along the fuel lines. Fuel quantity gauging systems with these relatively large and bulky transducers are heavy and require several connection points with the tank.

An improved fuel-monitoring system for an aircraft would eliminate the need, for pressure sensors and their associated pressure ports, and would have minimal or no contact with the fuel. It would be less susceptible to electromagnetic interference (EMI), and could also detect damage to the fuel tank or to the fuel-gauging system. The fuel-tank gauging system would benefit from a fuel-height or fuel-level measurement system that is small, compact and light, resulting in considerable weight and space savings.

It is desirable to provide an integrated fuel-tank system that overcomes the deficiencies and obstacles of capacitive fuel-gauging sensors for monitoring fuel levels in fuel tanks.

SUMMARY OF THE INVENTION

One aspect of the invention provides a fuel-tank system. The system includes a fuel tank, a transducer carrier tape embedded into the fuel tank structure, and at least one ultrasonic transducer attached to the transducer carrier tape. Ultrasound signals transmitted from at least one ultrasonic transducer are reflected from a fuel-air surface, and reflected signals are received by at least one ultrasonic transducer to determine the fuel level in the fuel tank.

The transducer carrier tape may be a flex circuit or a flex tape. The transducer carrier tape may be embedded in the base of the fuel tank. A separation barrier such as one or more plies of a composite material may cover the transducer tape to isolate the transducer carrier tape from fuel in the fuel tank. A controller may be connected to the transducer carrier tape and at least one ultrasonic transducer. The fuel level in the fuel tank is determined by measuring a transit time between the transmitted ultrasonic signals and the reflected signals from at least one of the ultrasonic transducers, and using the speed of sound in the fuel to determine the fuel level.

Another aspect of the invention is a method of determining fuel level in a fuel tank. Fuel level in the fuel tank may be determined by sending an ultrasonic signal from an interior surface of the fuel tank, receiving a reflected signal from a fuel-air surface in the fuel tank, and determining the fuel level based on the ultrasonic emission and the reflected signal. The ultrasonic emission may be sent from one of a plurality of ultrasonic transducers embedded in the base of the fuel tank. The fuel level may be determined by measuring the transit time between the ultrasonic signals and the reflected signal. The reflected signal may be received at one or more of the embedded ultrasonic transducers. The fuel temperature may be measured and used to compensate the fuel level determination.

Another aspect of the invention is a method of manufacturing a fuel tank with an ultrasonic fuel-level measurement system. A transducer carrier tape with at least one ultrasonic transducer is positioned against an interior surface of the fuel-tank shell, and the transducer carrier tape is encased with a separation barrier.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings.

BRIEF DESCRIPTION OF THE DRAWINGS

Various embodiments of the invention are illustrated by the accompanying drawings of various embodiments, wherein:

FIG. 4 is a block diagram of a method of manufacturing a fuel tank with an ultrasonic fuel-level measurement system, in accordance with one embodiment of the current invention.

DETAILED DESCRIPTION OF THE PRESENTLY PREFERRED EMBODIMENTS

Figure 1:
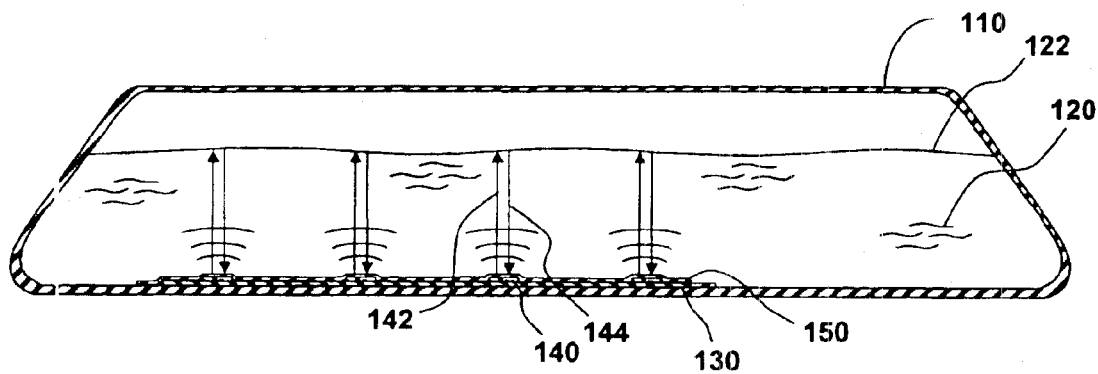
FIG. 1 is an illustration of a fuel-tank system for an aircraft, in accordance with one embodiment of the current invention.

FIG. 1 illustrates an instrumented fuel-tank system, in accordance with one embodiment of the present invention at 100. Fuel-tank system 100 comprises a fuel tank 110 containing fuel 120, a transducer carrier tape 130 with one or more ultrasonic transducers 140, and a separation barrier 150.

Fuel tank 110 is a containment vessel for fuel 120, which may include, for example, gasoline, fuel oil, or jet fuel. In one embodiment for use in jet aircraft, fuel tank 110 may, for example, hold 50 gallons of fuel or less for use in smaller, propeller-driven general aviation craft, or in excess of 10,000 gallons for larger commercial and military aircraft. Fuel tank 110 may be located in a wing, a fuselage, or any suitable location within the aircraft. Fuel tank 110 may be filled or partially filled with fuel. A partially filled fuel tank 110 may have a fuel-air surface 122 at the interface between fuel 120 and air or other gaseous materials comprising the un-filled portion of fuel tank 110.

Various materials may be used to construct fuel tank 110 such as composite materials including fiberglass or graphite epoxy. Fuel tank 110 may include a composite material. Composite materials typically include two constituents: fibers and a matrix. High tensile-strength fibers are dispersed throughout the matrix to provide additional strength, augmenting the toughness and chemical inertness of the matrix material. Typical matrix systems and fiber materials may include one of the following:

Typical Types of Matrix (Resin) Systems for Composites
  Thermoset Matrix Resin:
    Bismaleimide
    Cyanate Ester
    Epoxy, 250 cure
    Epoxy, 350 cure
    Toughened Epoxy
    Phelonic
    Polyester
    Polyimide
    Vinyl Ester
  Thermoplastic Matrix resin:
    Liquid Crystal
    Polyamide
    Polyamide-imide
    Polyarylene Ketone, Sulfide
    Polyether Ketone Family (PEK, PEKK, PEEK)
    Polyetherimide
    Polyethersulfone
    Polyimide
    Polyphenylene Sulfide Typical Types of Fibers for Composites
  Carbon Fibers from Precursors:
    Carbon Fiber from PAN
    Carbon Fibers from Pitch
    Carbon Fibers from Rayon
  Organic Fibers:
    Aramid (Kevlar)
    Carbon, PAN-based
    Carbon, pitch-based
    Carbon, Rayon-based
    Polybenzimidazole
    Polyethylene
  Inorganic Fibers:
    Structural high-strength Fiber Glass
    E-Fiber Glass
    Aluminum
    Boron
    Quartz
    Silicon Carbide
    Other Ceramics The tanks may be a single piece and of unitary construction, or assembled from several smaller pieces.

Transducer carrier tape 130 is coupled to a surface of fuel tank 110. Transducer carrier tape 130 may be attached to or embedded in one of the walls of fuel tank 110 such as the base or top. Transducer carrier tape 130 may be attached to the interior or the exterior of the tank. Transducer carrier tape 130 may be attached to a wall of the tank and covered with tank material to embed it inside the tank wall. Transducer carrier tape 130 contains one or more ultrasonic transducers 140 mounted or attached to the tape.

Transducer carrier tape 130 may comprise a flex circuit or a flex tape. Transducer carrier tape 130 is generally a flexible tape or circuit, containing ultrasonic transducers 140 and one or more layers of electrical traces within the tape. Transducer carrier tape 130 may be a flex circuit or a flex tape, comprising ultrasonic transducers and interconnections on one or more metal layers such as, for example, copper, aluminum or gold, separated by one or more passivation layers such as, for example, polyimide. Flex tapes and flex circuits are typically thin, multi-layer flexible circuit boards that contain one or more active or passive electronic devices, vias between metal layers, and solder pads for attaching any active or passive electronic devices. The flex tapes and flex circuits may be formed in various shapes such as short strips, long strips, interconnecting strips, rectangular sections, circular segments, or any combination thereof. The transducers, interconnects, traces, connectors, and any other circuit elements may be positioned on transducer carrier tape 130 as desired to provide indications of fuel height or fuel level.

Ultrasonic transducers 140 are positioned along transducer carrier tape 130 at one or more transducer pads. One or more ultrasonic transducers may be located at each transducer pad. The location of ultrasonic transducers 140 is determined by the tank geometry and orientation of the tank in the aircraft. Ultrasonic transducers 140 may be located at one or more places in the tank, such as the top and bottom, or various places along the bottom. Multiple ultrasonic transducers 140 provide additional signals for more accuracy in fuel-level determination, and add reliability and redundancy. Ultrasonic transducers 140 may-be positioned along the width or length of fuel tank 110 to provide multiple fuel-level measurements such that an average fuel-level can be determined.

At least one ultrasonic transducer 140 emits and sends an ultrasonic signal 142 into fuel 120. At fuel-air interface 122, the sound wave partially reflects and the reflected ultrasonic signal or reflected signal 144 travels back through the fuel to ultrasonic transducers 140. Reflected signal 144 is received by at least one ultrasonic transducer 140 to determine a fuel level in the fuel tank. Ultrasonic transducer 140, when deformed by reflected signal 144, typically generates a voltage or a charge. The generated voltage or charge can be used to determine fuel level by an ultrasonic fuel-gauge controller.

Separation barrier 150 may be disposed on transducer carrier tape 130 to cover or encase it, and to insulate or isolate transducer carrier tape 130 from fuel in the fuel tank. Separation barrier 150 also separates fuel 120 from connective traces within transducer carrier tape 130. Separation barrier 150 may be placed on top of transducer carrier tape 130 after the tape is attached to the inside or outside of the fuel tank. Separation barrier 150 may comprise a composite material. Separation barrier 150 may be formed from the same material used to form the tank, thereby embedding transducer carrier tape 130 within the tank wall. Ultrasonic emissions from ultrasonic transducers 140 may traverse a portion of the tank wall before propagating through fuel 120. The time required for traversing the walls of the tank may be subtracted when determining the fuel level.

Figure 2:
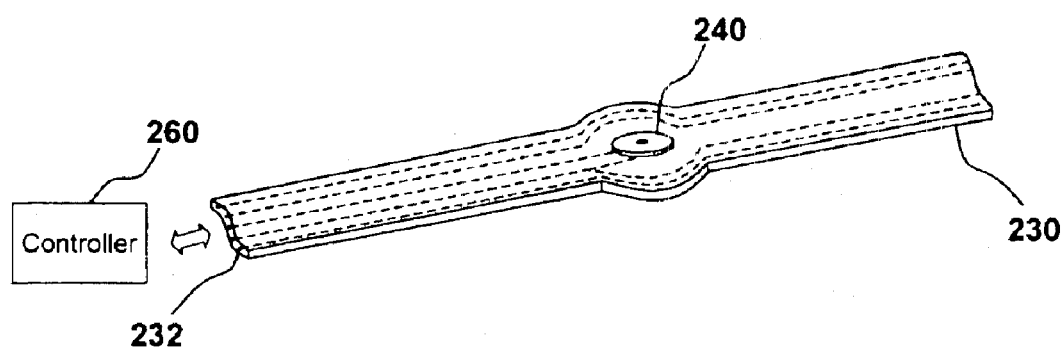
FIG. 2 is an illustration of a transducer carrier tape with an ultrasonic transducer, in accordance with one embodiment of the current invention.

FIG. 2 shows an illustration of a transducer carrier tape with an ultrasonic transducer for ultrasonic fuel-gauging measurements, in accordance with one embodiment of the present invention at 200. Ultrasonic fuel-gauging system 200 comprises a transducer carrier tape 230 and at least one ultrasonic transducer 240. An ultrasonic fuel-gauging system controller 260 is shown connected to ultrasonic fuel-gauging system 200.

Transducer carrier tape 230 includes at least one layer of interconnection wiring or traces 232, and at least one ultrasonic transducer 240 attached to the tape. Traces 232 provide electrical connections to ultrasonic transducers 240 along the tape. Traces 232 may be located on one or more metal layers of transducer carrier tape 230, formed by, for example, patterning and etch steps, as is well known in the art. The traces may include thin, narrow strips of copper, beryllium copper, nickel, tin, stainless steel, aluminum or gold sandwiched between thin, insulative layers of polyimide, polyester, mylar or other suitable polymeric material. One or more traces may be connected to each ultrasonic transducer 240. Traces 232 may be connected to each transducer on transducer carrier tape 230. Alternatively, one or more traces such as, for example, a common drive signal or a common ground may be connected in common to all the transducers along the tape. An additional set of traces may be included for the return signal, or the return signals may be sent back along the same set of traces used to drive the transducers. Other active and inactive components such as termination resistors and decoupling capacitors may also be mounted to transducer carrier tape 230. Drive circuitry and signal conditioning circuitry configured using standard or custom integrated circuits may be mounted on transducer carrier tape 230, such as on a transducer pad in close proximity to each ultrasonic transducer 240. Traces 232 may be used to connect ultrasonic transducers 240 to controller 260.

Ultrasonic transducer 240 may include any suitable ultrasonic driver, receiver, or driver/receiver pair, such as, for example, a piezoelectric disk. The piezoelectric disk comprises a disk-shaped button of piezoelectric material. Ultrasonic transducer 240 is comprised of a piezoelectric material such as lead zirconate titanate (PZT), a lead-free piezoelectric ceramic, quartz, zinc oxide, or a piezoelectric polymer such polyvinylidene fluoride (PVDF). Electrical contacts are made to the top and bottom of the disk. At least one ultrasonic transducer 240 is attached to transducer carrier tape 230. Ultrasonic transducers 240 may be attached to transducer carrier tape 230 and traces 232 using various solders, conductive epoxies, and adhesives, as are known in the art.

A voltage applied across the piezoelectric material generates an internal electric field and causes the piezoelectric material to contort. Rapid expansions and contractions of the piezoelectric material generate acoustic waves. The generated acoustic waves or acoustic emissions propagate from the ultrasonic transducer through any separation barrier or tank wall and into the tank. The acoustic waves may traverse through the fuel or through the air in the tank until a fuel-air surface is struck. A transmitted portion of the acoustic wave continues in the same direction, whereas a reflection portion returns back towards the ultrasonic transducer. When the reflected portion strikes an ultrasonic transducer, a charge or voltage is generated by mechanical deformations of the transducer. The signals may be sent directly through traces 232 to controller 260, or the signals may be locally conditioned near the transducer and then sent to controller 260 or another suitable signal processing system. An electrical connector and other electrical coupling devices such as a wire harness or multi-conductor cable (not illustrated) may be used to connect transducer carrier tape 230 to controller 260.

Controller 260 is operably connected to at least one ultrasonic transducer 240. Controller 260 includes electronic circuitry and timing circuitry to measure the transit time between the acoustic emission and the reflected signal from at least one of the ultrasonic transducers. The transit time or time-of-flight of the acoustic signal through the fuel or air in the tank is used to determine the fuel level. Fuel parameters such as the speed of the acoustic sound waves in the media are applied to the transit-time data to determine the fuel height or fuel level in the tank. Small changes in the speed of sound with fluid temperature or pressure may be compensated for with controller 260. One or more temperature sensors may be included on transducer carrier tape 230 such as near each ultrasonic transducer to provide accurate, local measurements of fuel temperature. Controller 260 provides output in any suitable digital or analog format for display and recording, for example, in the cockpit of a commercial or military aircraft equipped with a system of integrated fuel tanks.

Figure 3:
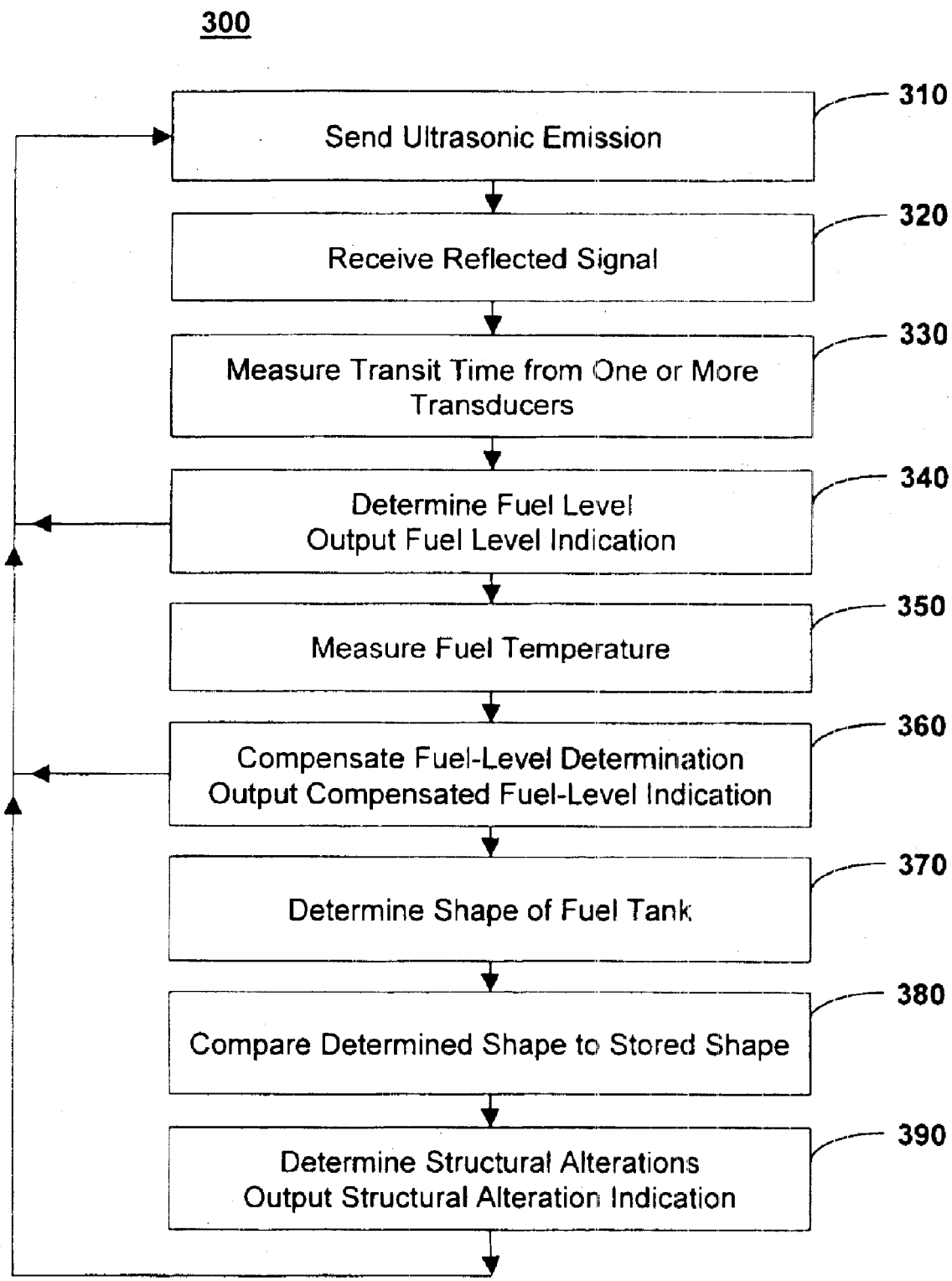
FIG. 3 is a block diagram of a method for determining fuel level in a fuel tank of an aircraft, in accordance with one embodiment of the current invention.

FIG. 3 shows a block diagram of a method of determining fuel height or fuel level in a fuel tank, in accordance with one embodiment of the present invention at 300. Fuel-level determination method 300 comprises steps to determine fuel level within an ultrasonic fuel-tank system.

An ultrasonic emission is sent from an interior surface of the fuel tank, as seen at block 310. The ultrasonic emissions traverse any portion of the fuel-tank wall and then propagate into the fuel or air in the fuel tank. One or more ultrasonic transducers mounted to or embedded within a wall of the fuel tank may generate ultrasonic emissions. The ultrasonic transducers are attached to a transducer carrier tape such as a flex circuit or a flex tape. Ultrasonic transducers such as piezoelectric disks are electrically connected to the flex circuit or flex tape. A plurality of ultrasonic transducers may be positioned along a flex circuit or a flex tape. The flex circuit or flex tape includes one or more layers of metallic interconnections. The transducer carrier tape may be attached to or embedded within an interior surface or an exterior surface of the tank wall. For example, the transducer carrier tape may be attached to the bottom of the fuel tank and covered with a separation barrier. Ultrasonic signals may be sent from one of a plurality of ultrasonic transducers embedded in the base portion of the fuel tank. Alternatively, the transducer carrier tape with a plurality of ultrasonic transducers may be attached to or embedded in the top surface of the fuel tank, with ultrasonic emissions propagating through any portions of the fuel-tank wall in front of the transducers and into the air in the fuel tank.

An ultrasonic emission from at least one ultrasonic transducer is reflected from a fuel-air surface, and a reflected signal from the fuel-air surface is received by at least one ultrasonic transducer to determine the fuel level in the fuel tank. The reflected signal may be received at one or more ultrasonic transducers on the transducer carrier tape. The ultrasonic emission may travel through the fuel to the fuel-air surface and back to the generating transducer or other transducer along the transducer carrier tape. Alternatively, the ultrasonic emission may travel through the air in the tank, reflect off the fuel-air surface, and travel back to the generating transducer or another transducer on the transducer carrier tape. The ultrasonic emissions may be generated and sent from one or more ultrasonic transducers on the transducer carrier tape. A controller or other suitable electronic interface may be used to generate the drive voltages to initiate the ultrasonic, emissions from the ultrasonic transducers.

A reflected signal is received from the fuel-air surface in the fuel tank, as seen at block 320. The reflected signal may be received at one or more ultrasonic transducers along the transducer carrier tape. The ultrasonic transducers generate a charge or a voltage when compressed or elongated by the ultrasonic waves, and the charge or voltage is used to determine when the reflected signal is received.

The transit time between the sent ultrasonic emission and the received reflected signal is measured, as seen at block 330. The transit time, also referred to as time-of-flight, is the time elapsed for an ultrasonic wave to have been sent from a transducer, traveled through the fuel and received back to one or more transducers. The transit time may be measured for sound propagation from one of a plurality of ultrasonic transducers to one of a plurality of ultrasonic transducers along the transducer carrier tape. Alternatively, the transit time may be measured for sound propagation between one transducer and itself, or between one or more ultrasonic transducer transceiver pairs. The transit time may be measured for sound-wave propagation from one ultrasonic transducer to multiple ultrasonic transducers. The transit time for sound-wave propagation through any intervening fuel-tank wall material may be subtracted out or calibrated out of the time-of-flight or transit time determination.

The fuel level of fuel within the fuel tank is determined based on the sent ultrasonic emission and the received reflected signal, as seen at block 340. The fuel level may be determined by measuring the transit time between the sent ultrasonic emission and the received reflected signal. The fuel level may be determined by measuring one or more transit times between the sent ultrasonic emissions and a plurality of received reflected signals from one or more of ultrasonic transducers embedded in a base portion of the fuel tank. In one embodiment, the fuel level is determined by multiplying the speed of sound of the acoustic wave through the fuel by the transit time, and dividing by two to account for two passages of the acoustic wave through the medium. Other methods of fuel-level determination may be made from the transit times, such as use of look-up tables or other suitable algorithms. Average fuel-height measurements may be made from multiple consecutive transit time measurements by averaging the transit-time measurements and determining the fuel level. The average transit time can then be multiplied by the speed of sound and divided by two to determine the fuel level. Alternatively, a look up table or other algorithm may be used to determine fuel height. Alternatively, the fuel level may be determined by averaging the transit times from more than one transducer, and determining the fuel level from this average transit time. Measurements from more than one ultrasonic transducer on the transducer carrier tape may provide more accuracy, compensating for the tank rolling and banking with turns, altitude adjustments, and shifts in velocity of the aircraft.

The fuel-height or fuel-level determinations may be made within a controller containing a central processing unit, memory with microcode for running the algorithm, and other software and hardware for determining fuel level. The controller and its associated hardware and software can process information from the fuel level determination into a suitable format for display and recording purposes. An indication of the fuel level may be output or updated when the fuel level has been determined. Indications of fuel level may be made by providing digital or analog signals from the controller that indicate the fuel level in a format compliant with any applicable fuel system standards.

Measurements of fuel level may be made with the controller and the ultrasonic transducers on a continuous basis, at pre-determined times, upon external request, or some combination thereof, by repeating blocks 310, 320, 330 and 340 accordingly.

Slight shifts in the speed of sound in a fluid occur with changes in temperature. Temperature variations can affect the accuracy of the fuel-level measurements. Compensation of fuel level can be made by measuring the fuel temperature of fuel in the fuel tank, as seen at block 350, and compensating the fuel-level determination based on the fuel temperature, as seen at block 360. Fuel temperature may be measured directly with a temperature sensor such as a thermocouple or resistive temperature device (RTD) in the fuel tank, or inferred from temperature measurements at or near the outside of the fuel tank. RTDs or other suitable temperature-sensing devices may be included on the transducer carrier tape with the ultrasonic transducers. The temperature-compensated fuel-level indication may be output or updated accordingly. Additional measurements of fuel level are possible by repeating blocks 310 through 360. Temperature-compensated fuel level indications may be output on a continuous basis, at pre-determined times, upon external request, or some combination thereof.

An approximation of the shape of the fuel tank may be determined based on the sent ultrasonic emissions and the received reflected signals from one or more ultrasonic transducers when the fuel tank is full of fuel, as seen at block 370. The determined shape may be compared to a stored shape of the fuel tank, as seen at block 380. Structural alterations of the fuel tank such as dents or bulges may be determined based on the determined shape and the stored shape of the fuel tank, as seen at block 390. For example, measures of transit times for each transducer representing the shape of the tank may be made and stored when the tank is full of fuel. At a subsequent time when the tank is again full of fuel, an additional set of transit times may be measured and compared to the stored values. A check may be made to determine if any of the additional set of transit times is altered appreciably from the stored values.

An indication of structural alterations may be output when the determined shape and the stored shape materially differ. Alternatively, a structural alteration indication may be output when it has been requested by an external system or inquiry. Additional indications of structural alterations may be determined and output on a continual basis, at predetermined times, upon external request, or some combination thereof.

FIG. 4 shows a block diagram of a method of manufacturing a fuel tank with an ultrasonic fuel-level measurement system, in accordance with one embodiment of the present invention at 400. Fuel-tank manufacturing method 400 comprises steps to manufacture a fuel tank for an aircraft with an integrated fuel-level measurement system.

A fuel-tank shell is provided, as seen at block 410. The fuel-tank shell may be provided as a unitary piece, or in sections or segments that are assembled together. The fuel-tank shell may be comprised of materials that are strong, tough, non-metallic and chemically resistant to airplane and jet fuels. The fuel-tank shell may comprise a composite material. Materials such as graphite epoxy, fiberglass, and other suitable composite materials with high-strength fibers in a tough matrix are typically used. Laminated sheets of composite material with embedded fibers may be glued together and shaped to form the tank walls. Uncured composite materials or composite materials with an evaporative solvent may be spread upon or applied to a form or mold of the tank, and dried or cured to provide a fuel tank with the desired shape and strength.

A transducer carrier tape with one or more ultrasonic transducers is positioned against a surface of the fuel-tank shell, as seen at block 420. The transducer carrier tape comprises a flex circuit, a flex tape, or any suitable flexible circuit board or tape. The ultrasonic transducers may be positioned as desired inside the tank or outside the tank, at the bottom of the tank or at the top of tank, or against any suitable surface of the fuel-tank shell.

The transducer carrier tape may be encased with a separation barrier, as seen at block 430. The separation barrier may partially or fully encase the carrier tape. The ultrasonic transducers may be covered with the separation barrier or left exposed. The separation barrier may be formed from one or more plies or layers of composite material. Each ply may be added on top of the transducer carrier tape, suitably adhered, and dried or cured. Alternatively, uncured composite material may be applied with any suitable application means such as brushing, painting, spraying, dispensing or rolling, and then dried or cured. Provision may be made for an electrical connector, a slot for the transducer carrier tape, or other suitable structure to get the electrical signals to and from the ultrasonic transducers.

While the embodiments of the invention disclosed herein are presently preferred, various changes and modifications can be made without departing from the spirit and scope of the invention. The scope of the invention is indicated in the appended claims, and all changes that come within the meaning and range of equivalents are intended to be embraced therein.

What is claimed is:

1. A fuel-tank system comprising:
    a fuel tank;
    a transducer carrier tape coupled to a surface of the fuel tank;
    at least one ultrasonic transducer attached to the transducer carrier tape, wherein an acoustic emission from at least one ultrasonic transducer is reflected from a fuel-air surface and a reflected signal is received by at least one ultrasonic transducer to determine a fuel level in the fuel tank; and
    a separation barrier disposed on the transducer carrier tape, wherein the separation barrier isolates the transducer carrier tape from fuel in the fuel tank.

2. The system of claim 1 wherein the fuel tank comprises a composite material.

3. The system of claim 1 wherein the transducer carrier tape comprises one of a flex circuit or a flex tape.

4. The system of claim 3 wherein the transducer carrier tape comprises at least one layer of metallic interconnections.

5. The system of claim 1 wherein the transducer carrier tape is embedded in a base of the fuel tank.

6. The system of claim 1 wherein the ultrasonic transducer comprises a piezoelectric disk.

7. The system of claim 1 wherein the separation barrier comprises a composite material.

8. The system of claim 1 further comprising:
    a controller operably connected to the at least one ultrasonic transducer, wherein the fuel level in the fuel tank is determined by measuring a transit time between the acoustic emission and the reflected signal from at least one of the ultrasonic transducers.

9. A method of determining fuel level in a fuel tank, the method comprising:
    sending an ultrasonic emission from an interior surface of the fuel tank;
    receiving a reflected signal from a fuel-air surface in the fuel tank;
    determining the fuel level based on the sent ultrasonic emission and the received reflected signal;
    measuring the fuel temperature of fuel in the fuel tank; and
    compensating the fuel level determination based on the fuel temperature.

10. A method of determining fuel level in a fuel tank, the method comprising:
    sending an ultrasonic emission from an interior surface of the fuel tank;
    receiving a reflected signal from a fuel-air surface in the fuel tank;
    determining the fuel level based on the sent ultrasonic emission and the received reflected signal;
    determining a shape of a fuel tank based on the sent ultrasonic emission and the received reflected signal, the fuel tank being full of fuel;
    comparing the determined shape of the fuel tank to a stored shape of the fuel tank; and
    determining a structural alteration of the fuel tank based on the determined shape and the stored shape of the fuel tank.

11. A fuel-tank system comprising:
    a fuel tank;
    a transducer carrier tape coupled to a surface of the fuel tank, the transducer carrier tape comprising one of a flex circuit or a flex tape, and the transducer carrier tape comprising at least one layer of metallic interconnections; and
    at least one ultrasonic transducer attached to the transducer carrier tape, wherein an acoustic emission from at least one ultrasonic transducer is reflected from a fuel-air surface and a reflected signal is received by at least one ultrasonic transducer to determine a fuel level in the fuel tank.

12. The method of claim 9 further comprising:
    communicating a signal characteristic of the reflected signal via a transducer carrier tape.

13. The method of claim 9 wherein the ultrasonic emission is sent from one of a plurality of ultrasonic transducers embedded in a base portion of the fuel tank.

14. The method of claim 13 wherein the plurality of ultrasonic transducers are positioned along one of a flex circuit or a flex tape.

15. The method of claim 9 wherein determining the fuel level comprises measuring a transit time between the sent ultrasonic emission and the received reflected signal.

16. The method of claim 9 wherein determining the fuel level comprises measuring a plurality of transit times between the sent ultrasonic emission and a plurality of received reflected signals from a plurality of ultrasonic transducers embedded in a base portion of the fuel tank.

17. The method of claim 9 further comprising:
    determining a shape of a fuel tank based on the sent ultrasonic emission and the received reflected signal, the fuel tank being full of fuel;
    comparing the determined shape of the fuel tank to a stored shape of the fuel tank; and
    determining a structural alteration of the fuel tank based on the determined shape and the stored shape of the fuel tank.

* * * * *